United States Patent [19]

Holmes

[11] Patent Number: 5,415,661

[45] Date of Patent: May 16, 1995

[54] IMPLANTABLE SPINAL ASSIST DEVICE

[75] Inventor: David C. Holmes, Boca Raton, Fla.

[73] Assignee: University of Miami, Miami, Fla.

[21] Appl. No.: 36,501

[22] Filed: Mar. 24, 1993

[51] Int. Cl.$^6$ ............................. A61F 5/24; A61F 2/44
[52] U.S. Cl. ......................................... 606/69; 623/17
[58] Field of Search ....................... 623/16, 18, 15, 17; 606/69

[56] References Cited

U.S. PATENT DOCUMENTS

| 4,512,038 | 4/1985 | Alexander et al. | 623/18 |
| 4,743,260 | 5/1988 | Burton . | |
| 4,834,757 | 5/1989 | Brantigan . | |
| 4,878,915 | 11/1989 | Brantigan . | |

FOREIGN PATENT DOCUMENTS

| 0013862 | 8/1980 | European Pat. Off. | 606/69 |
| 9013265 | 11/1990 | WIPO | 606/69 |

OTHER PUBLICATIONS

A. A. White et al., "Spinal Stability: Evaluation and Treatment", *American Academy of Orthopaedic Surgeons Instructional Course Lectures*, vol. 30, pp. 457–483, C. V. Mosbly, 1981.

Frymoyer et al., "Segmental Instability: Rational for Treatment", *Spine*, 10:280–286, 1985.

A. Naylor, "The Biomechanical Changes in the Human Intervertebral Disc in Degeneration and Nuclear Prolapse", *Orthopaedic Clinics of North America*, 2:343, 1971.

U. Ebeling et al., "Microsurgical Reoperation Following Lumbar Disc Surgery Timing, Surgical Findings, and Outcome in 92 Patients", *Journal of NeuroSurgery*, 70:397–404, 1989.

A. A. White et al., *Clinical Biomechanics of the Spine*, Philadelphia, J. P. Lipponcot, Co., 1978.

R. Quinell et al., "Pressure Standardized Lumbar Discography", *British Journal of Radiology*, 53:1031–1036, 1980.

C. K. Lee et al., "Lumbosacral Spinal Fusion–A Biomechanical Study", *Spine*, vol. 9, No. 6, 1984, pp. 574–581.

J. W. Frymoyer, "A Comparison of Radiographic Findings in Fusion & Non-Fusion Patients Ten or More Years Following Lumbar Disc Surgery", *Spine*, vol. 4, No. 5, pp. 435–440.

J. Dvorak et al., "The Outcome of Surgery for Lumbar Disc Herniation—I. A 4–17 Years' Follow-Up with Emphasis on Somatics Aspects", *Spine*, vol. 13, No. 12, pp. 1418–1422, 1988.

A. A. White, "Overview of and Clinical Perspective on Low-Back Pain Syndrome", *Spine Update 1984*, edited by H. K. Genant, San Francisco, Radiology Research and Education Foundation, 1984, pp. 1–3.

H. B. Skinner, "Composite Technology for Total Hip Arthroplasty", *Clin. Ortho. and Rel. Res.*, No. 235, pp. 224–236, Oct. 1988.

D. A. Nagel et al., "Stability of the Upper Lumbar Spine Following Progressive Disruptions and the Application of Individual Internal and External Fixation Devices", *JBJS*, vol. 63-A, No. 1, Jan. 1981, pp. 62–70.

M. S. Pearcy et al., "Axial Rotation and Lateral Bending in the Normal Lumbar Spine Measured by Three-Dimensional Radiography", *Spine*, vol. 9, No. 6, 1984, pp. 582–587.

P. C. McCaffe, "Device Related Osteoporosis With Spinal Instrumentation", Spine, 14(9), pp. 919–926.

W. H. Kirkaldy-Willis et al., "Toward a More Precise Diagnosis of Low Back Pain", *Spine Update 1984*, pp. 5–16.

*Primary Examiner*—David Isabella
*Attorney, Agent, or Firm*—Watov & Kipnes

[57] ABSTRACT

An implantable device for restoring normal biomechanical function to a motion segment unit of the spine which includes a curvilinear body composed of a composite material made up of a fiber material interspersed in a matrix material.

11 Claims, 4 Drawing Sheets

IMPLANTABLE SPINAL ASSIST DEVICE

FIELD OF THE INVENTION

The present invention is generally directed to implantable prosthetic devices and particularly to an implantable device for supporting and reconstructing a motion segment unit (spine joint) of the spine in such a manner that normal biomechanical function is restored.

BACKGROUND OF THE INVENTION

It is well known that low-back pain is one of the most frequently occurring and expensive disabling ailments, especially for patients in the 30–60 year age bracket. Although low-back pain syndrome is a very common occurrence, its diagnosis to this day is very difficult.

The vertebral column (spine) is a biomechanical structure composed primarily of ligaments, muscles, vertebrae and intervertebral discs. The biomechanical functions of the spine include i) support of the body (trunk and appendages), which involves the transfer of the weight and the bending movements of the head, trunk and arms to the pelvis and legs, ii) complex physiologic motion between these body parts, and iii) protection of the spinal cord and the nerve roots.

The major regions of the spine are the cervical, thoracic, lumbar and sacral. The vertebrae increase in size and mass from the cervical to the lumbar regions. The increase in size of the vertebrae is directly related to an increased capacity for supporting larger loads. The lumbar region is therefore the major load bearer of the spine. However, this increase in load bearing capacity is paralleled by a decrease in flexibility. Because the lumbar region bears heavier loads than other regions of the spine, the lumbar trunk (low back structure) is more susceptible to strain and hence low-back pain.

The spine is comprised of a series of joints known as motion segment units (MSU). The motion segment unit is the smallest component of the spine that exhibits kinematic behavior characteristic of the entire spine. The motion segment unit is capable of flexion, extension, lateral bending and translation. The components of each motion segment unit include two adjacent vertebrae and their apophyseal joints (facet capsules), the intervertebral disc and the connecting ligamentous tissue. Each component of the MSU contributes to the mechanical stability of the joint.

The facet capsules, for example, are bony elements which help support compressive loads (approximately 20%) and resist torsional motion. The intervertebral disc, composed of the nucleus pulposus (a gel-like hydrodynamic ball bearing located at the center of the disc) and annulus fibrosus (concentric collagen fibers oriented at 30 degrees to one another and encapsulating the nucleus pulposus) gives the spinal column resilience and the ability to withstand compression, rotation and bending strains. Forces directed axially are absorbed by the nucleus pulposus and transmitted radially allowing for them to be absorbed by the fibers of the annulus fibrosus. In addition to the support provided by the facet capsules and the intervertebral disc, the ligaments, uniaxial elements which support loads in tension, are crucial in assuring the structural integrity of the spine. Each of the seven ligaments contained in a lumbar spine motion segment unit (intertransverse ligament, posterior longitudinal ligament, anterior longitudinal ligament, ligamentum flavum, capsular ligament, interspinous ligament, and supraspinous ligament) aids in assuring spinal stability by limiting excessive range of motion and absorbing energy that is applied as a result of trauma.

Many causes of low-back pain are attributed to the instability of the motion segment unit. According to A. A. White et al., "Spinal Stability: Evaluation and Treatment", *American Academy of Orthopaedic Surgeons Instructional Course Lectures*, Vol. 30, pp. 457–484, C. V. Mosbly, 1981, segmental instability is defined as "the loss of ability of the spine under physiologic loads to maintain relationships between vertebrae in such a way that there is neither damage nor subsequent irritation to the spinal cord or nerve roots, and, in addition there is no development of incapacitating deformity or pain due to structural changes". In other words, instability is an abnormal response to applied loads characterized by motion in the motion segment unit beyond normal constraints. Excess motion can be abnormal in quality (i.e. abnormal coupling patterns) or in quantity (abnormal increased motion) or both. Excess motion results in damage to the nerve roots, the spinal cord, and other spinal structures.

The underlying causes of the structural changes in the motion segment unit leading to instability are trauma, degeneration, aging, disease (tumor, infection, etc.), surgery, or a combination thereof. It is known that a mechanically unstable motion segment unit can originate due to degeneration of the nucleus pulposus. A degenerate nucleus leads to disc space narrowing, loss of viscoelastic properties and the subsequent transfer of compressive loads to the annulus fibrosus. The altered anatomic dimensions and subsequent abnormal response to loading can cause loss of pre-tension in the ligamentum flavum, and longitudinal ligaments, degeneration of the facet capsules (and possible subluxation) with a consequence of secondary degenerative osteoarthritis of the joints.

Current surgical techniques employed in spine surgery require the removal of ligaments and bone, in addition to sections of the intervertebral disc. The result of such procedures diminish the structural integrity of the spine joint. As can be seen by the work of D. A. Nagel et al., "Stability of the Upper Lumbar Spine Following Progressive Disruptions and the Application of Individual Internal and External Fixation Devices", *JBJS* Vol. 63-A, No 1, January, 1981, pp. 62–70, disruption of the supraspinous and interspinous ligaments, ligamentum flavum, and the facets at L1–2 increases the range of motion in Flexion-Extension, Lateral Bending, and Axial Rotation by 4.1 degrees (48.8% increase), 0.8 degrees (16.32% increase), and 1.4 degrees (63.63% increase) respectively. Disruption of the posterior longitudinal ligament, posterior annulus, and lateral annulus in addition to the above, increase the average range of motion in Flexion-Extension, Lateral Bending, and Rotation by 8.9 degrees (105.95% increase), 3.4 degrees (69.39% increase) and 12.4 degrees (563% increase) respectively over the intact case alone.

An unstable motion segment unit may be fused to form a permanent or rigid internal fixation of all or part of the intervertebral joints using such materials as rods, hooks, metallic mesh, plates, bolts, screws and/or cement. However, permanent spinal fixation is a difficult surgical technique due to the irregular shape of the bones, the relative weakness of most of the bones of the vertebrae and the complexity and strength of the deforming muscular forces acting on the trunk.

The need for a compliant or flexible spinal implant is evidenced in three prominent factors: (i) reoperations required for patients having undergone spinal decompressive surgery (including discectomies), (ii) further MSU degeneration in patients with fusions and internal fixation, and (iii) MSU instability resulting from the surgical procedure, in patients not normally indicated for fusion.

The re-operation of patients having undergone spinal decompressive surgery is of concern as a significant number of long-term failures may be evidenced. For example, J. W. Frymoyer et al., "Segmental Instability: Rational for Treatment", *Spine*, 10:280–287, 1985, undertook a study to compare the long-term effects of surgery on lumbar disc disease when treated by disc excision alone or by disc excision combined with primary posterior midline fusion. The study demonstrated a high percentage of unsatisfactory results in patients who had either simple disc excision or disc excision combined with spinal fusion. Thirty percent (30%) of patients whose spines were fused and 38% of those patients whose spines were not fused were considered long-term failures because of persistent symptoms or the need for reoperation.

In addition to the long-term failures of disc excision with or without fusion, the use of internal fixation with fusion following disc excision has shown no increase in success rate. A. A. White et al., *Clinical Biomechanics of the Spines*, Philadelphia, J. P. Lipponcot, Co., 1978, reported on the first ten years of a prospective study on herniated lumbar disc patients who underwent surgery. The results indicated that the addition of a fusion with internal fixation after a bilateral laminectomy and disc excision did not increase the subjective or objective success rate. Fair to poor results were seen in 22% of the patients with no fusion and 42% of the patients with fusion.

In lieu of the success/failure rates of these procedures, other underlying mechanical phenomena may contribute to the further degeneration of the spine's motion segment units. Radiographic findings suggest that spinal fusion imposes new stresses on the vertebral motion segment above the fusion. R. Quinnell et al., "Pressure Standardized Lumbar Discography", *British Journal of Radiology*, 53:1031–1036, 1980, and C. K. Lee et al., "Lumbosacral Spine Fusion—A Biomechanical Study", *Spine* Vol. 9, No. 6, 1984, pp. 574–581, found alterations of the mechanics at adjacent levels when experimental floating lumbar fusions were performed on cadaver spines. The concern about increased mechanical stress at adjacent motion segments has been reinforced by clinical reports of lumbar spinal stenosis at the motion segment immediately above lower lumbar spine fusions and acquired spondylolysis at the cephalad vertebra in the fusion mass. Therefore, fusion generates a conflict between immediate benefit and late consequences.

In the course of surgical management of a herniated disc, the surgeon must dissect the supraspinous and interspinous ligaments as well as other soft tissue to expose and remove the herniated mass. While no studies have been organized to determine the contribution of surgically induced MSU instability, data concerning the incidence of re-operation at the same level in those patients not fused at the time of surgery indicates there is a relationship. J. Dvorak et al., "The Outcome of Surgery for Lumbar Disc Herniation—I. A 4–17 Years' Follow-up with Emphasis on Somatic Aspects", *Spine* Vol. 13, No. 12, pp. 1418–1422, 1988, found that in 362 patients follow-up 4–17 years after surgery indicated almost 50% of the patients considered their long-term results unsatisfactory. Moreover, A. A. White, "Overview of and Clinical Perspective on Low-Back Pain Syndrome", *Spine Update* 1984, edited by HK Genant, San Francisco, Radiology Research and Education Foundation, 1984, pp. 127–130, estimates the international average for recurrence at the same lumbar level at 15%.

The current management of spinal fusion may include the use of rigid metallic rods and plates. These systems have been used regularly since the early 1960's, first for the management of scoliosis, and then for the management of low-back disease. Current systems are attached either by means of a hook or by pedicle screws. In all cases, the device is intended to rigidly immobilize the motion segment unit to promote fusion. Due to its inherent rigid design (as compared to the surrounding bone), these devices have often caused localized osteoporosis at the attachment sites P. C. McCaffee, "Device Related Osteoporosis With Spinal Instrumentation", *Spine*, 14(9), pp. 919–926, (stress shielding due to the rigidness of the implant), and have directly and indirectly contributed to the degeneration of the joints above and below the fusion site as well as at the fusion site itself (see R. Quinell et al. and C. K. Lee et al.). Due to their material composition, these stainless steel devices have frequently been rejected by patients in response to the release of metal ions. Furthermore, the ferromagnetic properties of the implant material itself has prevented the use of post-operative MRI or CT scan imaging due to scatter of the image.

In the design of such implants, several criteria must be taken into consideration. These criteria include the modulus of the implant material, the geometry and dimensions of the device as well as the biocompatibility or inertness of the implant material. The modulus of elasticity of the material may be expressed as the ratio of material stress (force per unit area) to strain (% elongation). Materials with a higher modulus will exhibit less elongation when exposed to the same stress than those materials of lower modulus and as such will appear stiffer.

The geometry and dimensions of the device will dictate implant performance in accordance with accepted mathematical concepts. Implant geometry will be used in describing the mathematical model of the implant. Implant dimensions will be used to help quantitate the model. For example, implant dimensions will help quantitate the cross-sectional moment of inertia which can be described as $\pi r^4/4$ for a rod-like element.

The biocompatibility of the implant material is essential in implant design as to prevent the "poisoning" of the patient as well as to prevent a biological response which may corrode the implant material. Not only must the material be biocompatible, but it must be suited for load bearing applications in the body.

Examples of proposed spinal implants include Burton, U.S. Pat. No. 4,743,262, which discloses a stabilization system for a vertebral column in which the posterior vertebral elements are removed to enable attachment of bar-like elements to adjacent vertebra. The supporting bars can be fabricated from a carbon reinforced plastic.

While providing some flexibility and support, the device disclosed in Burton is disadvantageous because it removes the posterior elements (facet capsules) which provide about 20% of the support inherent of the spine as well as torsional stability for the joint. Removal of the posterior elements reduces the amount of support available for the affected motion segment unit. In addition, linear bar-like elements cannot provide support and movement which closely approximates the function of the motion segment unit.

Other examples include Brantigan, U.S. Pat. Nos. 4,834,757 and 4,878,915, where systems are disclosed for the support of the vertebral column through the use of plugs to be placed in the disc space. The first device disclosed by Brantigan is a biocompatible composite cage whose intended use is to contain either autologous or allograft bone and promote fusion of the vertebral bodies.

While the device disclosed by the Brantigan '757 patent will provide compressive support to the spinal column, it is a rigid support and as such does not allow for normal joint motion. Moreover, the role of the device diminishes as the surrounding vertebral bone integrates into the bone contained within the cage.

The Brantigan '915 patent discloses a solid device having barbs for biting into the bone as well as spaces between the barbs intended to be sites of bone ingrowth. Again, as in the '757 patent, the aforementioned device is intended to promote fusion of vertebral bodies thereby eliminating any motion within that spine joint.

Therefore, based on clinical evidence suggesting the incidence of long-term failures and incidence of further degeneration at the levels adjacent to the fusion site, and the limitations posed by using rigid metallic systems, there is a need for an implantable prosthetic device which can restore normal biomechanical function to an injured or diseased motion segment unit by reducing the load on the existing vertebral disc and facet joints or capsules. Such a device would be compliant or flexible and allow for joint motion in six-degrees of freedom, yet, would limit motion beyond that which has been determined to be unphysiologic.

SUMMARY OF THE INVENTION

The present invention is generally directed to an implantable compliant or flexible spine implant for restoring normal biomechanical function to a motion segment unit of the spine and for preventing further degeneration leading to instability and consequential lower back pain and/or permanent damage to the neural elements. Unlike current rigid metallic implants whose purpose is to promote fusion of the spine joint, the aforementioned device is intended to perform as a reconstructive prosthesis allowing for normal motion while supporting the spine joint such that any remaining soft tissue may heal or further damage to that soft tissue be prevented. The support provided by the compliant implant in conjunction with the support of the existing soft tissues is intended to replicate the physiologic response of a healthy motion segment unit.

The present compliant implant restores normal motion between the vertebrae and the surrounding motion segment units by supporting and distributing a percentage of the load normally carried by the affected motion segment unit to the surrounding motion segment units. As the compliant implant is a three-dimensional implant, support will be provided in three-dimensions. For example, the increased range of torsional motion as evidenced by mechanical instability will be managed by the torsional resistance of the compliant implant. Thus, rotary instability resulting from partial or complete removal of the facets and disc, will be managed to acceptable limits. As a consequence, further degeneration of the affected motion segment unit and disc will be prevented.

The compliant implant of the present invention comprises a curvilinear body composed of a composite material comprising a fiber material interspersed in a matrix material preferably selected from biocompatible thermosetting polymers, thermoplastic polymers, alloys, mixtures thereof and the like. Means are provided at the respective ends of the curvilinear body for securing the device to adjacent vertebrae.

The curvilinear body is designed and composed of materials which in combination provide a compliant implant which closely approximates the normal movement of the spine. The compliant implant of the present invention functions as a shock absorber to reduce the impact of excessive loads on the affected motion segment unit of the spine by transferring some of the load to adjacent motion segment units and by limiting excessive range of motion.

In accordance with the present invention, the compliant implant may be customized according to the needs of the individual patient. For example, by varying the layer to layer fiber volume and/or orientation of the fibers within the composite laminate structure and/or by varying the degree of curvature of the central section of the implant, an implant may be constructed that may vary from fully compliant to relatively stiff implants depending on system parameters. The support provided by the compliant implant in conjunction with the support provided by the surviving soft tissue will approximate the support provided by a healthy MSU.

BRIEF DESCRIPTION OF THE DRAWINGS

The following drawings in which like reference characters indicate like parts are illustrative of embodiments of the invention and are not intended to limit the invention as encompassed by the claims forming part of the application.

DETAILED DESCRIPTION OF THE INVENTION

Figure 1A:
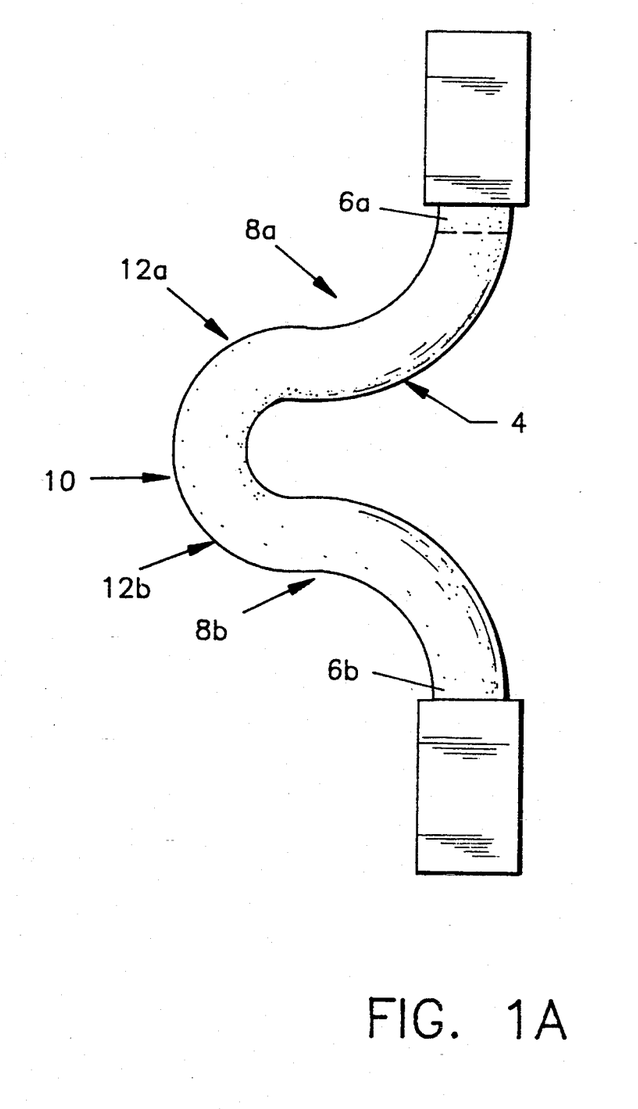
FIG. 1A is a side view of one embodiment of the implantable compliant implant in accordance with the invention.

Referring to the drawings and particularly to FIG. 1A, there is shown an implantable compliant implant 2 having a body 4 and respective ends 6a and 6b. The body has a curvilinear shape including terminal sections 8a, 8b, central section 10 and intermediate sections 12a, 12b which lie between the ends 6a, 6b and the central section 10. Each end 6a, 6b has attached thereto a means for securing the compliant implant 2 to the vertebral column as described hereinafter.

The curvilinear body 4 is preferably made of a composite material having superior strength and fatigue characteristics while having a relatively low modulus of elasticity as compared to metals. A composite material is one formed from two or more materials which exhibit performance characteristics exceeding that of the individual components alone.

The loading conditions the compliant implant will experience in the lumbar spine will vary depending on patient height and weight. However, based on the work of M. S. Pearcy et al., "Axial Rotation and Lateral Bending in the Normal Lumbar Spine Measured by Three-Dimensional Radiography", Spine, Volume 9, No. 6, 1984, pp.582–7, the compliant implant system can be expected to limit axial rotation to 2 degrees for L1–2 (lumbar motion segment units 1 and 2), L2–3, and L5–S1 (sacral motion segment unit 1), and 3 degrees for L3–4 and L4–5. For lateral bending, the compliant implant system can be expected to limit lateral bending to 10 degrees for L1–2, 11 degrees for L2–3, 10 degrees for L3–4, 6 degrees for L4–5 and 3 degrees for L5–S1.

The composite materials employed in the present invention preferably incorporate a fiber material interspersed in a matrix material preferably composed of a thermosetting and/or a thermoplastic polymer.

The preferred fiber materials are selected from carbon or polyamide fibers. Carbon fibers are produced, for example, by drawing a fiber of a polymer such as polyacrylonitrile from a melt or solution and then carbonizing it after various heat treatments (e.g. AS4 made by Hercules, Inc., Magna, Utah). Techniques for producing carbon fibers are well known and customarily employed in the art.

Polyamide fibers, particularly aromatic polyamides such as poly[paraphenylene terephthalamide] (e.g. Kevlar made by DuPont Chemical, Wilmington, Del., have a fairly rigid chain structure. In production, the polymer molecules are aligned along the fiber axis, producing a high-modulus, high-tensile strength fiber. Carbon fibers are preferred for use in the present invention as the compressive strength of the fibers is almost five times that of the polyamide fibers.

Thermoplastic polymers, a typical matrix material for use in constructing a compliant implant, derive their strength from the chemical structure of the polymer and the tight interlocking of the long chains. These polymers soften and melt upon heating but do not decompose. While other matrix materials (e.g. thermosetting polymers, alloys, and the like) may be employed in the present invention, the preferred matrix materials are thermoplastic polymers, particularly polysulfone and polyetheretherketone, because they possess excellent biocompatibility characteristics, produce no scatter on CT scan or MRI imaging systems and can be post-formed following fabrication by the application of heat and pressure.

Polysulfone has a relatively high glass transition temperature (190° F.). It is iracoelastic, exhibits creep and stress relaxation and has excellent mechanical properties. Polyetheretherketone has a glass transition temperature of 143° F. It has excellent chemical resistance, wear resistance, fatigue resistance, flexural strength, and tensile strength and good gamma-radiation stability. Of the two commonly known biocompatible engineering thermoplastics, Polyetheretherketone is preferred because of its ability to perform as a load bearing material in a biological environment.

Methods of forming the composite material for use in the present invention are disclosed in H. B. Skinner, "Composite Technology for Total Hip Arthroplasty", Clin. Ortho. and Rel. Res., No. 235, pp. 224–236, October, 1988. In particular, the composite material may be formed by net compression molding via composite pre-peg tape placement, pultrusion, filament winding, braiding, and injection molding.

The method selected for forming the composite material is in part dependent on whether the load applied to the compliant implant will be distributed evenly in three planes (isotropic distribution) or focused more along a directional path (anisotropic).

The preferred method for producing composite materials for use in constructing the implantable compliant implant of the present invention is net compression molding via use of a composite pre-peg tape. Net compression molding entails the use of two molds, an outer mold and an inner mold. The outer mold is constructed of metal while the inner mold may be constructed of either metal or of a synthetic material such as silicone. Net compression molding provides highly consistent parts with controlled section dimensions and wall thicknesses. The process allows for precise hole locations/dimensions and is suitable for mass production.

While net compression molding may be used with a variety of thermoplastic types and configurations, the preferred configuration is that of a prepreg tape. A prepreg tape comprises unidirectional carbon fibers of a specified volume impregnated with a matrix material. The tape, of a predetermined width, may be cut to any length and placed within a mold at any desired orientation. Varying the fiber diameter, the number of prepreg layers and the percentage of fiber volume of the tape will ultimately dictate the properties of the composite material to be formed.

Net compression molding may be used to form either an anisotropic composite or an isotropic composite. To form an anisotropic composite via net compression molding, a prepreg film containing continuous carbon fibers impregnated in a thin film of a matrix is cut, oriented in the desired direction (as described by engineering analysis) and placed into the mold until the desired thickness (as described by the dimension of the mold) is obtained. The mold is then closed and heated under pressure until the thermoplastic component of each prepreg layer melts to produce a consolidated matrix with good adhesion to the reinforcing carbon fibers.

An isotropic composite may be formed in the manner as above except fiber orientation is distributed evenly in all directions and is not concentrated in any particular plane as is the case of the anisotropic composite. The term "quasi-isotropic" will herein be used to refer to orientations where the layer to layer orientation forms a part in which the prepreg is approximately evenly distributed in all three planes. Such nomenclature will be employed as the use of the prepreg layering technique produces a composite part which is approximately equally strong in all three directions as a whole (macroscopic scale), but on a layer to layer scale is anisotropic in nature (microscopic scale).

The compliant implant of the present invention can be fabricated with different degrees of stiffness (i.e. flexibility) to accommodate different degrees of joint degeneration. The flexibility of the compliant implant is dependent on the properties of the composite material and the geometry of the compliant implant itself. The compliant implant will be expected to load share and manage motion in flexion-extension (forward bending), lateral bending (side to side bending), and torsion (twisting). Depending on the degenerative condition of a MSU, the compliant implant will be fabricated to compensate for any loss of support in any plane. For example, Should loss of support be evidenced in six degrees of freedom or more specifically rotation, then a "quasi-isotopic" pre-peg layering process will be utilized. In other instances, an anisotropic layer to layer orientation will be utilized with emphasis on the planes requiring additional supplemental support. Loss of support in flexion-extension will be compensated by reinforcement in the sagittal plane, while loss of support in lateral bending will be compensated for by reinforcement in the frontal plane.

With respect to the composite material, flexibility is based principally on the layer to layer orientation of the carbon fibers within the composite laminate and the amount of the carbon fiber present (measured as a percent of the volume of the composite material) as well as the properties of the matrix material itself. In general, as the volume fraction of the carbon fiber increases, the strength and stiffness of the composite material will increase. It is important to note, however, that when the volume fraction of the fiber approaches 0% by volume, the strength of the composite material approximates the strength of the matrix material (e.g. thermosetting and/or thermoplastic polymers). As the volume fraction of fiber reaches a range of from about 40 to 70%, the strength of the fiber determines the strength of the composite and is roughly equal to the volume fraction of the fiber multiplied by the tensile strength of the fiber. On the other hand, if the fiber volume is increased to about 80% of the composite material, the density of the fibers will be so great that the individual fibers will begin to contact each other causing the transverse tensile strength to drop to zero.

It is preferred for most applications to provide a fiber volume in the range of about 40 to 70% by volume. Within this range, for example, an implant constructed from a pre-peg having a fiber volume of 40% would exhibit more compliance (springiness) than a similar implant constructed from a pre-peg having a fiber volume of 70%. Pre-peg tapes are readily available with standard fiber volumes of 60%.

Thus, in the direction of the fibers, the elastic modulus of the composite will approach that of the fibers as the amount of matrix decreases. The converse is also true, a composite with a small volume fraction of fiber has an elastic modulus similar to that of the matrix alone, although the stiffness is somewhat greater by virtue of the reinforcing effect produced by the small amount of fiber present.

The length of the fiber generally varies directly with the strength of the device (although, once the fibers reach a critical length, the strength remains the same). The fibers employed in the composite materials used in accordance with the present invention are typically continuous and unidirectional fibers. Discontinuous or short fibers, particularly those having a length of less than one millimeter, are typically used where an isotropic composite with stiffness distributed in more than one direction is desired (typically formed by injection molding, etc.). Ball bearings or other small parts would benefit from short fiber construction, while larger load bearing parts would benefit from continuous fiber construction.

In accordance with one embodiment of the present invention, the stiffness of the material at the terminal portions 8a, 8b of the device (as dictated by fiber orientation, volume, and geometry) generally exceeds that of the central section 10, and in another embodiment of the invention, the stiffness of the material continuously diminishes from the terminal sections 8a, 8b toward the central section 10.

The geometry of the compliant implant is also implicated in the degree of flexibility which may be imparted to the implant. The principal geometric component is the curvature of the central section 10 and intermediate sections 12a, 12b of the body. This curvature may be described by both the radius of the curve as well as the arc measure of the curve.

The geometry of the compliant implant and its accompanying motion may be approximated in two-dimensions by the ring spring equation. As shown with reference to FIGS. 1B and 1C, an applied load F is first transmitted by a vertical linear segment which then transfers the load to an essentially horizontal linear segment L. Subsequently, the load is transferred to the curved portion of the compliant implant along a curved arc having a radius R and an arc measure of $2\theta$. While FIG. 1A indicates a curved transition zone from the vertical linear segment to the horizontal linear segment (specifically terminal sections 8a and 8b), the predictions of the ring-spring equation herein refer to the spring-like element located in the central portion of the device (sections 10, 12a, and 12b). The contribution of the transition elements is believed to be negligible.

Figure 1B:
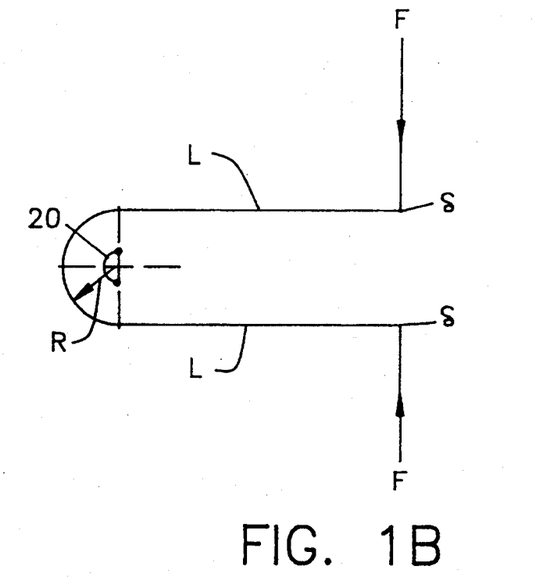
FIG. 1B is a schematic view similar to the embodiment shown in FIG. 1A illustrated to show various angular and force relationships.
Figure 1C:
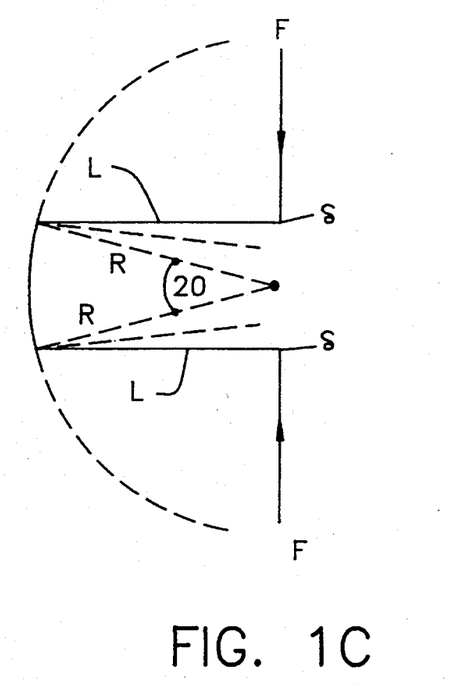
FIG. 1C is a schematic view similar to the embodiment shown in FIG. 1A illustrated to show various angular and force relationships. In this instance FIG. 1C differs from FIG. 1B in the type of curvature obtained by varying the radius of curvature and the arc measure.

Depending on the applied load F, the compliant implant will respond such that the linear segment L will deflect inwardly by a distance $\delta$ at the junction of L and F. The inward deflection $\delta$ may be represented by Equation (1):

$$\delta = \frac{dV}{dF} \quad (1)$$

where V is the total strain energy which may be represented by Equation (2):

$$V = \int_0^\theta \frac{[FL + FR \cos \theta]^2 R d\theta}{EI} + \int_0^L \frac{(FL)^2 dx}{EI} \quad (2)$$

wherein E is the modulus of elasticity of the composite material and I is the sectional moment of inertia of the implant body.

By assuming the arc of the spring to be 180°, for the sake of simplifying the differential equations, Equation (1) reduces to Equation (3) (note that in cases where an arc of curvature different than 180 degrees is required, Equation (3) would differ in that it represented a function integrated over a different range):

$$\delta = \frac{2FL^3}{3EI} + \frac{\pi R F L^2}{EI} + \frac{4FR^2L}{EI} + \frac{\pi FR^3}{2EI} \quad (3)$$

Furthermore, in the actual development of the implant, the member length L will be insignificantly small. Therefore, for the sake of simplicity, member length L, as realized along terminal sections 8a and 8b, will be assumed to be zero and Equation (3) can then be reduced to Equation (4):

$$\delta = \frac{\pi F R^3}{2EI} \quad (4)$$

where the radius of curvature of R for an arc of 180° is determined by Equation (5):

$$R = \sqrt[3]{\frac{2EI}{\pi \text{ Stiffness}}} \quad (5)$$

where Stiffness=force/displacement=$F/\delta$.

Moreover, the distance between the superior and inferior pedicles of a motion segment unit, is somewhat fixed as it falls within a finite physiologic range. Therefore, the length of the implant is also finite. More specifically, the distance across the central active spring element (sections 10, 12a, and 12b) will be a fixed distance regardless of desired stiffness. Both the radius of curvature and arc measure may be changed, though, but the resulting central spring element will have the same vertical length. For example, the geometries illustrated in FIGS. 1B and 1C show two implants each with a different radius of curvature and arc measure. The implant described in FIG. 1C, while having a greater radius of curvature, has a smaller arc measure and as such will show a greater degree of stiffness than the implant described in FIG. 1B. Generally, the spinal implants of the present invention will have an arc measure exceeding 0° up to 180° depending on the desired degree of stiffness.

As described, the radius of curvature and arc measure of the compliant composite implant will be a function of: (i) the desired stiffness of the implant, which is a function of the stiffness of the patient's MSU after the decompressing procedure which is a function of the integrity of the surviving tissues of the MSU as measured by a spinal stiffness gauge of the type disclosed in Mark D. Brown et al, U.S. Pat. No. 4,899,761, or a manual Kochler clamp test/technique; (ii) the modulus of elasticity E of the composite material; and (iii) the cross-sectional moment of inertia I of the implant.

The modulus of elasticity E is the only term in Equation (2) which changes as a result of a change in the type of composite material which is used in the compliant implant. The modulus of elasticity of the composite material is the degree to which a material deforms as a result of a given stress and is influenced by i) the type of matrix material used, ii) the volume of the fibers, iii) the length of the fibers, and iv) the orientation of the fibers within the matrix. Given a standard geometric configuration, changing the modulus of the composite by either altering the type of matrix, the volume of fiber, or both, would yield a part that resists motion to a greater or lesser degree.

Thus, the amount of deflection $\delta$ (the relative stiffness of the device) is directly related to the amount of strain energy which in turn is directly related to the degree of curvature (curve radius and arc measure) of the compliant implant and inversely related to the modulus and thickness of the composite material. Therefore, implant characteristics are dependent upon modulus of elasticity, material thickness, radius of curvature, and arc of curvature and can be varied by alterations in any and all of these parameters. For example, by decreasing the degree of curvature (increasing the radius of curvature and decreasing the arc measure) and holding all other parameters constant, additional stiffness is imparted to the device and the amount of deflection $\delta$ is reduced. Conversely, as the degree of curvature is increased, the relative stiffness of the device decreases. Similar changes may be seen by varying the modulus or thickness and holding the remaining parameters constant. For the compliant implant, the preferred method for varying stiffness is to alter the modulus of elasticity and hold implant thickness, radius of curvature, and arc of curvature constant.

In general, greater stiffness will be realized at the terminal sections 8a, 8b than the central section 10 of the implantable device 2 whereas greater strength will be required at the central section 10 as it will experience large bending loads. In a preferred form of the invention, there is a gradual decrease in stiffness from the terminal sections 8a, 8b and continuing through the intermediate sections 12a, 12b to the central section 10.

Choosing a suitable fiber orientation will depend on the particular requirements for the implantable device. If greater stiffness is required because of a significant degenerate condition of an affected motion segment unit, then a greater density of fibers or fiber orientation lay-up corresponding to greater stiffness will be used. It should be noted that the density and layer to layer orientation of the fibers may be selected such that the implantable device approximates a rigid implant. Conversely, if less support of the motion segment unit is required, then the volume fraction of the fibers can be reduced and an orientation of fibers chosen for the particular implant. Thus, the determination of the mechanical properties of the compliant implant may be evidenced in the implant's geometry (its shape and thickness), the type of materials used (modulus of elasticity) to construct the implant, the percent fiber volume, and the relative orientation of the fibers as they relate to one another.

Figure 2:
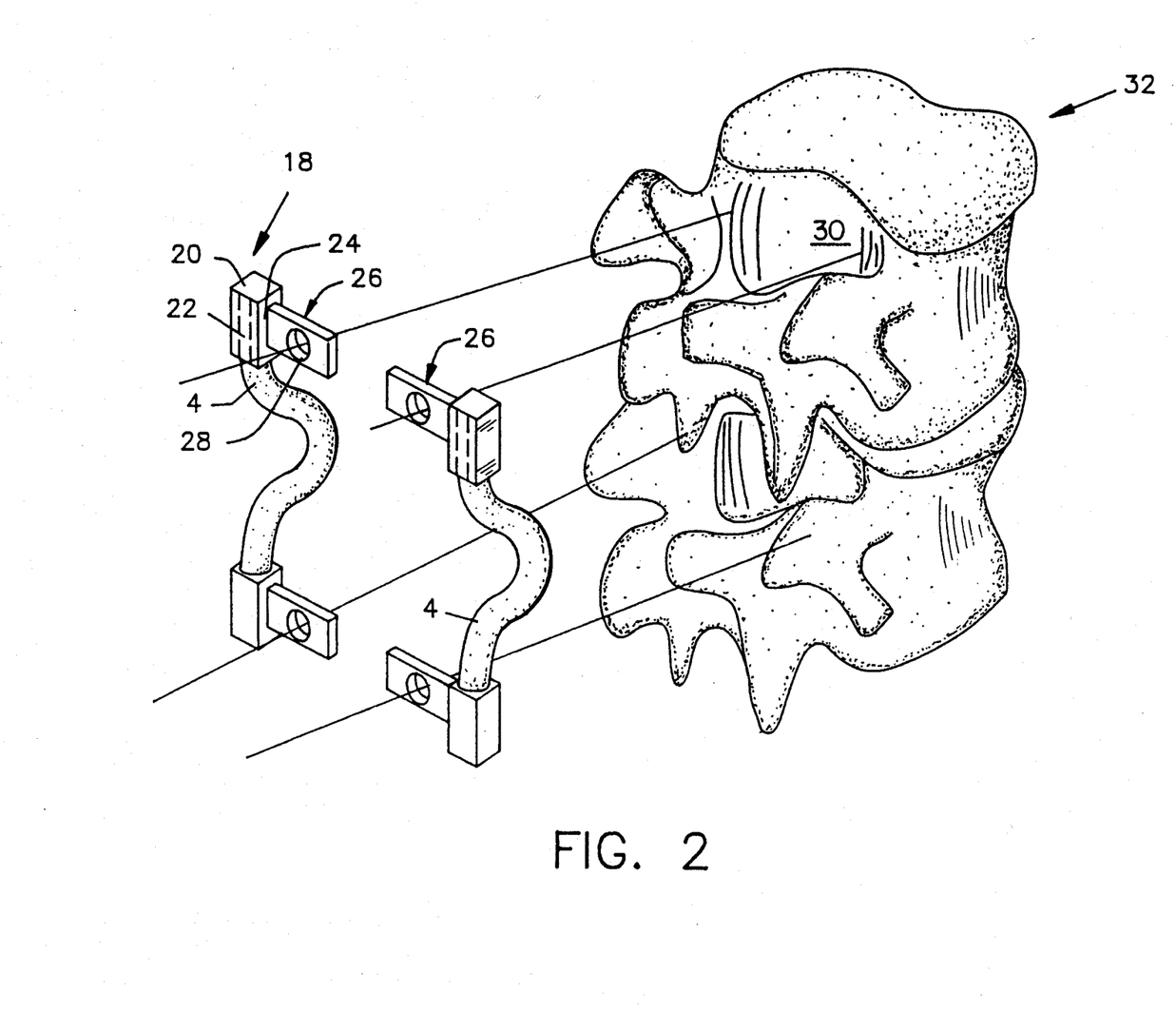
FIG. 2 is an exploded view of a pair of implantable compliant implants of the present invention for attachment to adjacent vertebrae.
Figure 3:
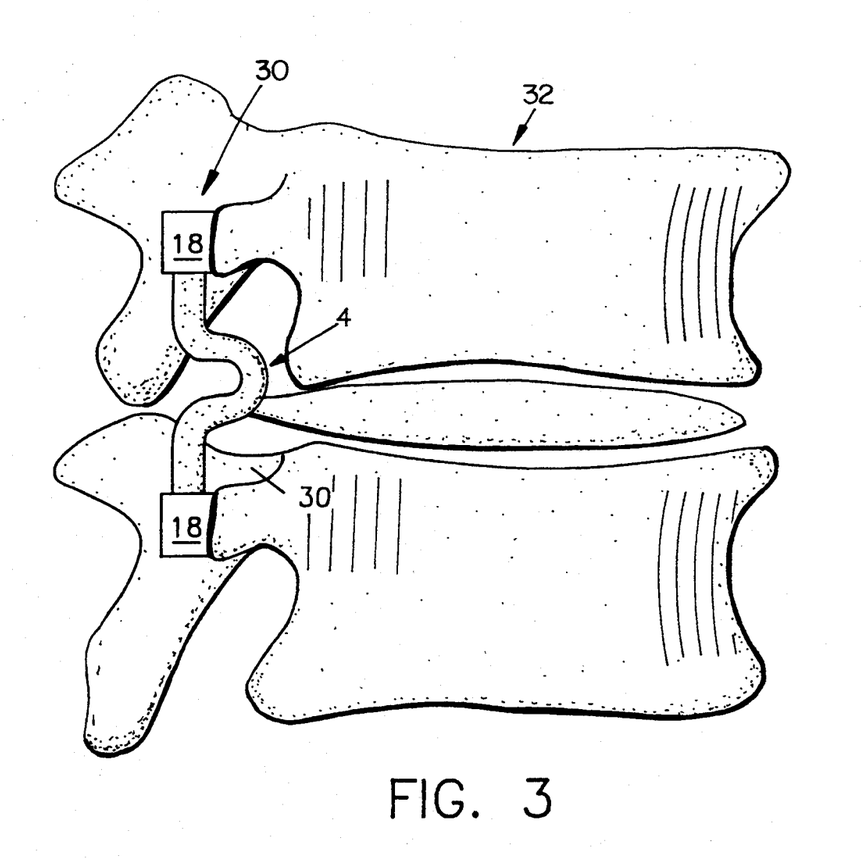
FIG. 3 is a side view of the motion segment unit shown in FIG. 2 with an implantable compliant implant of the invention secured thereto.

The implantable device is rendered operational by attachment to the pedicles of adjacent vertebrae. Referring to FIGS. 2 and 3, the device 2 has attached to its opposed ends 6a, 6b, a fastening element 18 comprised of a block 20 having a hole therein 22 for attachment of the curvilinear body 4. A second hole 24, essentially perpendicular to the hole 22 receives an extension 26 having a central through hole 28 therein. The hole 28 is adapted to receive a pedicle screw (not shown) for insertion into the pedicle 30 of a vertebrae 32. While pedicle screw attachment is preferred, the use of sublaminar hooks may also be employed.

Typically two implants are used to anchor a single motion segment unit (one on the left and one on the right). Accordingly, it is preferred to have the respective extensions 26 facing each other as shown specifically in FIG. 5. It should be noted that more than one pair of implants may be used to support the spine (each at different MSU levels), particularly when more than two vertebrae exhibit degenerative characteristics.

EXAMPLE

A compliant implant in accordance with the present invention is prepared in the following manner. A composite laminate formed material having a circular cross-section radius of 3 mm containing continuous fibers of carbon oriented at +/−45°, and an arc measure of 180° has a Modulus of Elasticity E of 21,600 N/mm². The cross-section Moment of Inertia I is determined by:

$$I = \frac{\pi r^4}{4} \text{ where } I = 20.25\pi$$

Given a normal motion segment unit of the lumbar region of the spine exhibiting a compressive stiffness of 1,000 N/mm, the compliant implant would have a radius of curvature of 9.56 mm as determined from Equation (5). Further changes in the radius of curvature can be made by altering the dimensions of the cross-sectional radius (making the device thicker or thinner), altering the arc measure, or by selecting a material having a different modulus of elasticity (e.g. a material with a different matrix/fiber ratio, fiber orientation, or a different matrix material). Given the formulas as shown above, a modulus of elasticity, or cross sectional radius may be solved for assuming all other parameters are known.

What is claimed is:

1. A compliant implantable device for restoring normal biomechanical function to a motion segment unit of the spine comprising a flexible body having a longitudinal axis, said body being curved along said longitudinal axis and being composed of a composite material comprising a fiber material interspersed in a matrix material, said body comprising a curved central section unattached to a motion segment unit and a pair of opposed terminal sections, each terminal section having respective end portions for attaching the implantable device to adjacent motion segment units, said central section being free to move in response to pressure applied to the motion segment unit to provide support for and restore normal biomechanical function to the motion segment unit.

2. The implantable device of claim 1 wherein the matrix material is selected from the group consisting of a biocompatible thermosetting polymers, thermoplastic polymers, alloys and mixtures thereof.

3. The implantable device of claim 1 wherein the fiber material is selected from biocompatible carbon fibers and polyamide fibers.

4. The implantable device of claim 2 wherein the matrix material is selected from polysulfone and polyetheretherketone.

5. The implantable device of claim 1 wherein the body is composed of the composite material in the form of a pre-peg tape.

6. The implantable device of claim 1 wherein the fiber material has an isotropic fiber orientation.

7. The implantable device of claim 1 wherein the fiber material has an anisotropic fiber orientation.

8. The implantable device of claim 1 wherein the density of the fiber material is from about 40 to 70% by volume based on the total volume of the composite material.

9. The implantable device of claim 1 wherein the body further comprises a pair of intermediate sections between each of said terminal sections and said central section, said intermediate sections having a lower stiffness than said terminal sections.

10. The implantable device of claim 9 wherein the stiffness of the device continuously decreases from the terminal sections to the central sections.

11. The implantable device of claim 1 wherein the body has an arc measure exceeding 0° and less than 180°.

* * * * *